United States Patent — Ocheltree

(10) Patent No.: US 10,295,457 B1
(45) Date of Patent: May 21, 2019

(54) AIRPLANE CABIN AIR QUALITY MONITORING SYSTEM

(71) Applicant: Larry Ocheltree, Huntersville, NC (US)

(72) Inventor: Larry Ocheltree, Huntersville, NC (US)

(*) Notice: Subject to any disclaimer, the term of this patent is extended or adjusted under 35 U.S.C. 154(b) by 76 days.

(21) Appl. No.: 15/620,884

(22) Filed: Jun. 13, 2017

(51) Int. Cl.
G01N 21/25 (2006.01)
G01N 21/27 (2006.01)
G01N 33/00 (2006.01)

(52) U.S. Cl.
CPC ......... *G01N 21/255* (2013.01); *G01N 21/274* (2013.01); *G01N 33/0031* (2013.01)

(58) Field of Classification Search
CPC .................................................. G01N 33/0031
See application file for complete search history.

(56) References Cited

U.S. PATENT DOCUMENTS

| 5,791,982 | A | 8/1998 | Curry | |
|---|---|---|---|---|
| 5,889,199 | A | 3/1999 | Wong | |
| 6,170,318 | B1* | 1/2001 | Lewis | G01N 27/126 340/632 |
| 6,201,245 | B1 | 3/2001 | Schrader | |
| 6,362,741 | B1 | 3/2002 | Hickox et al. | |
| 6,680,778 | B2 | 1/2004 | Hinnrichs et al. | |
| 6,791,088 | B1 | 9/2004 | Williams, II et al. | |
| 7,851,758 | B1 | 12/2010 | Scanlon et al. | |
| 8,899,097 | B2 | 12/2014 | Wu | |
| 8,938,973 | B2 | 1/2015 | Dooley et al. | |
| 2012/0212347 | A1* | 8/2012 | Boone | G08B 21/12 340/632 |

FOREIGN PATENT DOCUMENTS

| CN | 204463378 U | 7/2015 |
|---|---|---|
| FR | 2992723 A1 | 1/2014 |
| KR | 100866762 B1 | 10/2008 |
| WO | 2016189420 A1 | 12/2016 |

* cited by examiner

*Primary Examiner* — Tri T Ton
*Assistant Examiner* — Rufus L Phillips
(74) *Attorney, Agent, or Firm* — Kyle A. Fletcher, Esq.

(57) ABSTRACT

The airplane cabin air quality monitoring system comprises a gas monitor. The gas monitor measures the atmosphere within an aircraft for a plurality of potentially hazardous gases. The gas monitor further comprises a plurality of gas sensors, a plurality of compensation sensors, a spectrometer, and a control system. The plurality of gas sensors, the plurality of compensation sensors, the spectrometer, and the control system are electrically interconnected. The control system manages and regulates the operation of the gas monitor. The control system generates an alert if a potentially hazardous gas is detected. The airplane cabin air quality monitoring system further comprises a docking station stores the gas monitor when the gas monitor is not in use. The docking station: 1) recharges the battery of the gas monitor; and, 2) establishes a hardwired first communication link between the gas monitor and the ACARS of the aircraft.

16 Claims, 10 Drawing Sheets

AIRPLANE CABIN AIR QUALITY MONITORING SYSTEM

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of instruments including measurements and testing, more specifically, an instrument for analyzing the chemical properties of a gas.

By its nature, an aircraft is a confined space that: 1) does not allow for unconstrained entry or exit of passengers during operation of the aircraft; and, 2) does not allow for the free exchange of atmospheric gases between the interior and exterior of the aircraft during the operation of the aircraft. The confined space can further create a psychologically stressful environment wherein a passenger can become hypersensitive to real, or imagined, stimuli within the aircraft. One of the most difficult situations for a flight crew to handle is a passenger that "smells" something. Several factors become relevant in this situation: 1) the sense of smell is highly variable between individuals; 2) the sense of smell is affected by the psychological state of an individual; 3) the ability to breathe is a primary physiological requirement of all individuals thereby increasing the sensitivity of an individual to a smell within the confined space of the aircraft; and, 4) the expression of a concern about a smell by a selected passenger can negatively influence the level of psychological stress of those passengers in the vicinity of the selected passenger.

While not typically a problem, the nature of the confined space of an aircraft can occasionally cause the accumulation of potentially hazardous gases within the confined space of the aircraft making it difficult for a flight crew to convincingly dismiss the expressed concerns of a passenger. Clearly, a device that can: 1) monitor the atmosphere within an aircraft for potentially harmful gases; 2) be operated on an as needed basis by the flight crew; and, 3) can be used to test gases within a localized area within the aircraft would be of benefit to a flight crew attempting the alleviate the concerns of a passenger.

SUMMARY OF INVENTION

This disclosure addresses the needs of a flight crew as described above.

The airplane cabin air quality monitoring system is a handheld measurement device. The airplane cabin air quality monitoring system is configured for use within an aircraft. The airplane cabin air quality monitoring system is an integrated test device that measures the atmosphere with an aircraft for a plurality of potentially hazardous gases and provides immediate results of the measurements to the flight crew. The plurality of potentially hazardous gases comprises one or more chemical substances that are selected such that: 1) the chemical substance will be in a gas phase at normal temperature and pressure conditions; 2) there is a chemical mechanism that causes, or a significant occurrence probability that, the chemical substance can accumulate within the confined space of the aircraft; and, 3) the chemical substance is a substance about which health concerns may potentially exist.

The airplane cabin air quality monitoring system comprises a gas monitor. The gas monitor measures the atmosphere within an aircraft for the plurality of potentially hazardous gases. The gas monitor further comprises a plurality of gas sensors, a plurality of compensation sensors, a spectrometer, and a control system. The plurality of gas sensors, the plurality of compensation sensors, the spectrometer, and the control system are electrically interconnected. The control system manages and regulates the operation of the gas monitor.

The control system further collects the measurements taken by the plurality of gas sensors, the plurality of compensation sensors, and the spectrometer. Each of the plurality of gas sensors is a commercially available gas sensor that is dedicated to detecting a gas selected from the plurality of potentially hazardous gases. Because the readings of many of the plurality of gas sensors will vary in a known fashion with changes in environmental conditions, the control system uses the data collected from the plurality of compensation sensors to adjust the reported measurements to compensate for these environmental factors. Each of the plurality of compensation sensors comprises a sensor that is dedicated to measuring an environmental condition for this purpose.

The spectrometer is a failsafe mechanism that is incorporated into the gas monitor. Specifically, the spectrometer takes spectrometric readings of the atmosphere. The control system then: 1) compares the spectrometric readings with a previously provided standard for atmospheric air to determine if something unidentified is in the atmosphere; 2) generates an alert if something unidentified is detected in the atmosphere; and, 3) stores the spectrometric readings to allow for further analysis at a future date.

The airplane cabin air quality monitoring system further comprises a docking station that stores the gas monitor when the gas monitor is not in use. The docking station: 1) recharges the battery of the gas monitor; and, 2) establishes a hardwired first communication link between the gas monitor and the ACARS of the aircraft These together with additional objects, features and advantages of the airplane cabin air quality monitoring system will be readily apparent to those of ordinary skill in the art upon reading the following detailed description of the presently preferred, but nonetheless illustrative, embodiments when taken in conjunction with the accompanying drawings.

In this respect, before explaining the current embodiments of the airplane cabin air quality monitoring system in detail, it is to be understood that the airplane cabin air quality monitoring system is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the airplane cabin air quality monitoring system.

It is therefore important that the claims be regarded as including such equivalent construction insofar as they do not depart from the spirit and scope of the airplane cabin air quality monitoring system. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
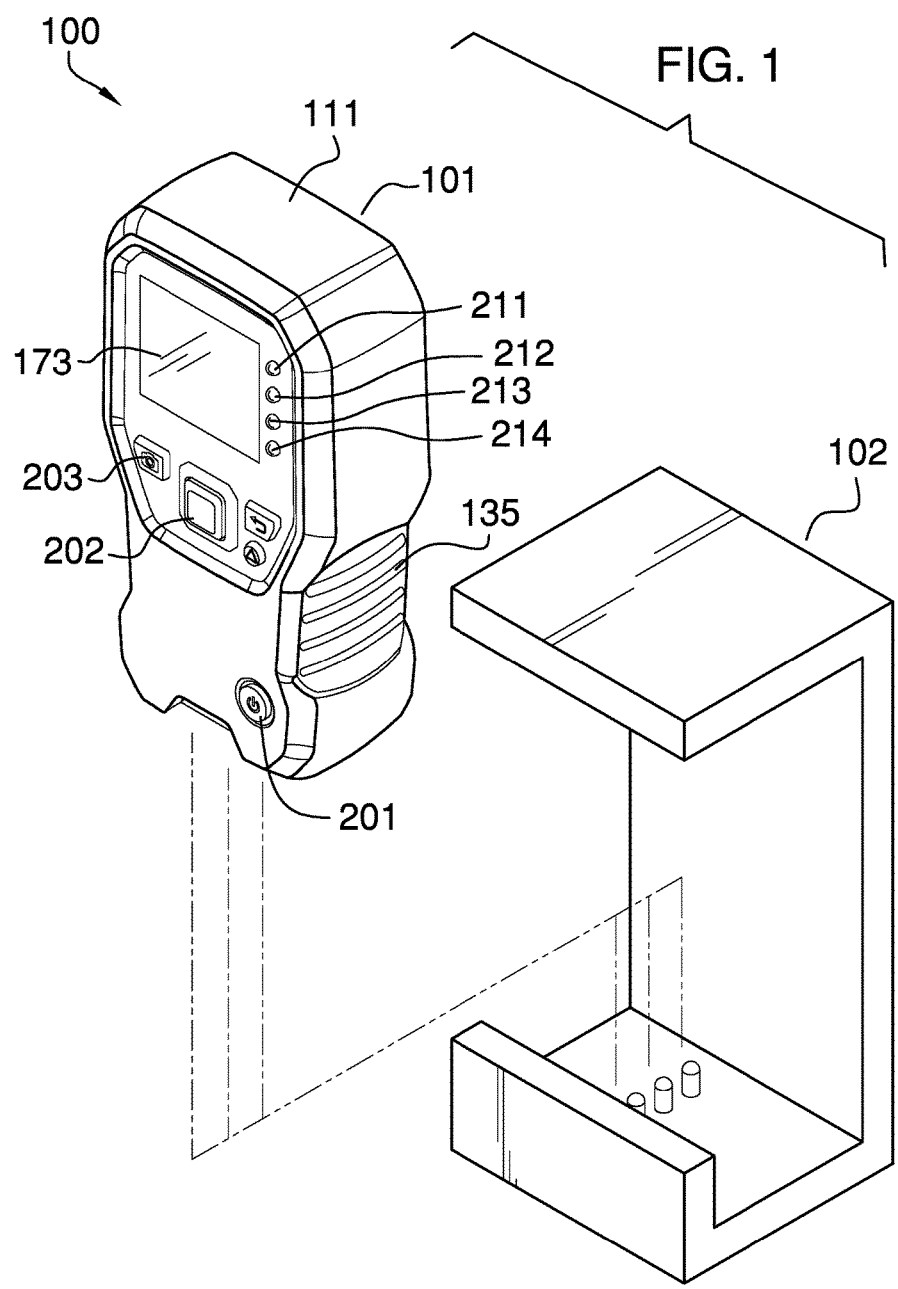
FIG. 1 is an exploded view of an embodiment of the disclosure.
Figure 2:
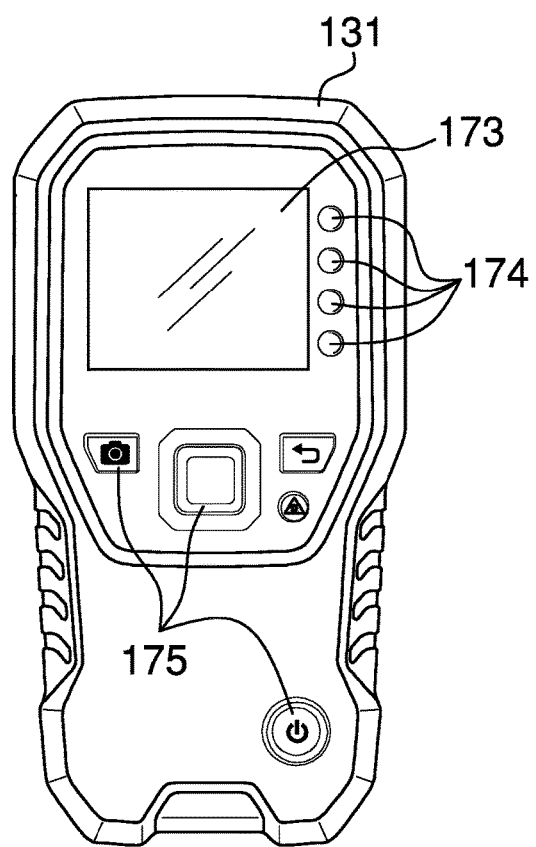
FIG. 2 is a front view of an embodiment of the disclosure.
Figure 3:
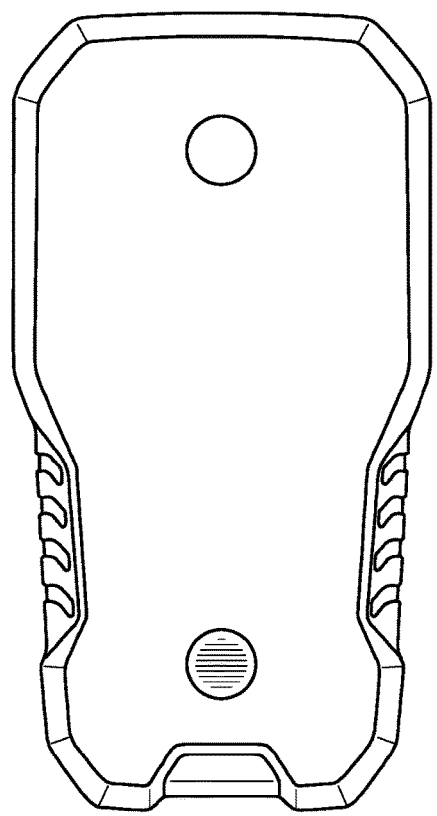
FIG. 3 is a rear view of an embodiment of the disclosure.
Figure 4:
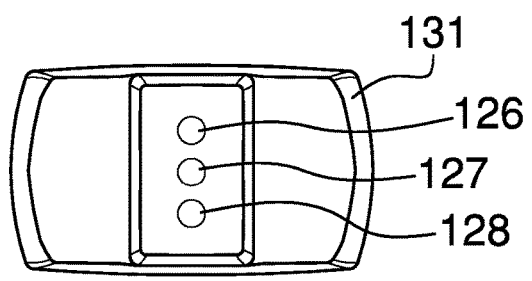
FIG. 4 is a bottom view of an embodiment of the disclosure.
Figure 5:
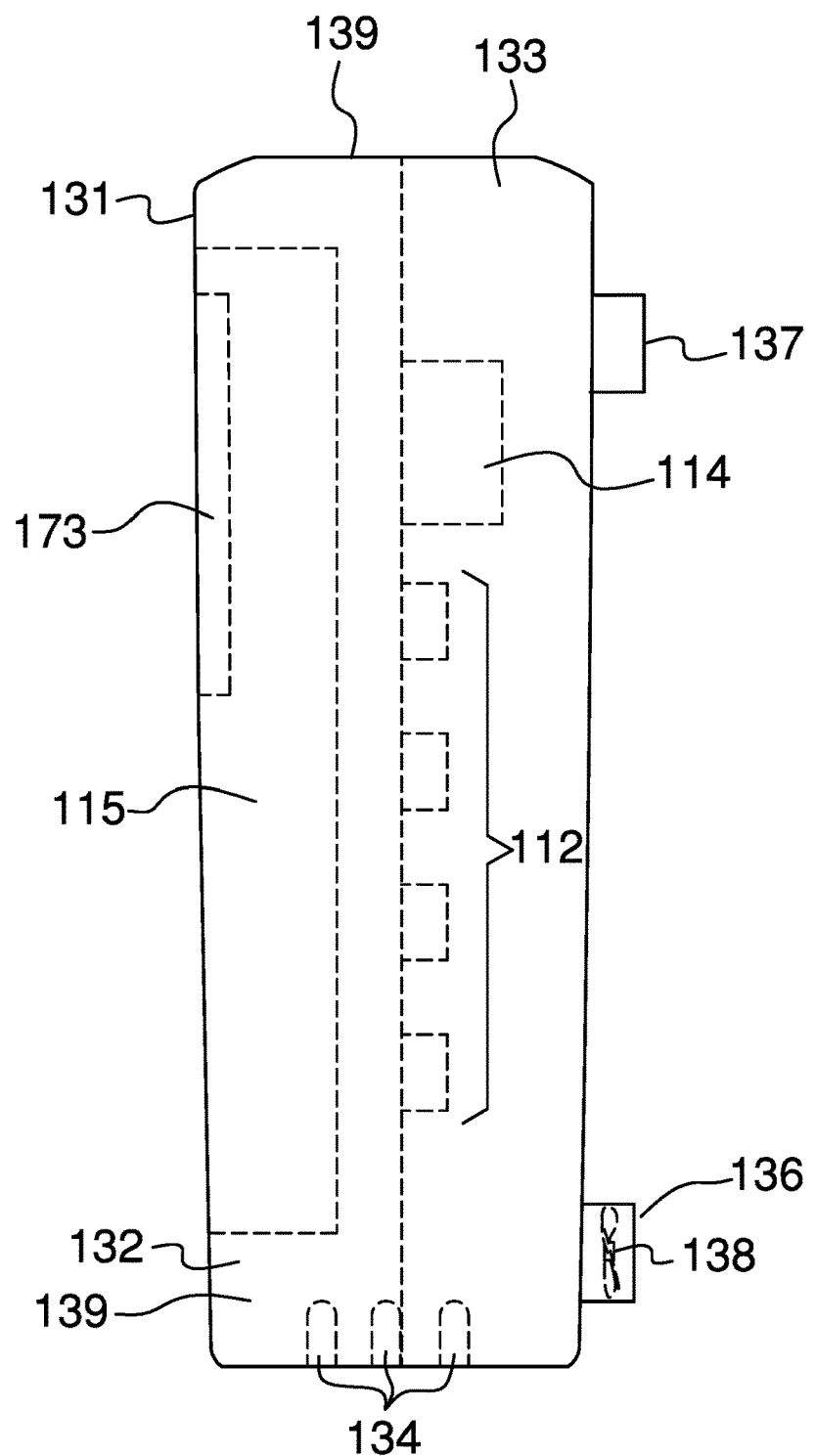
FIG. 5 is a side view of an embodiment of the disclosure.
Figure 6:
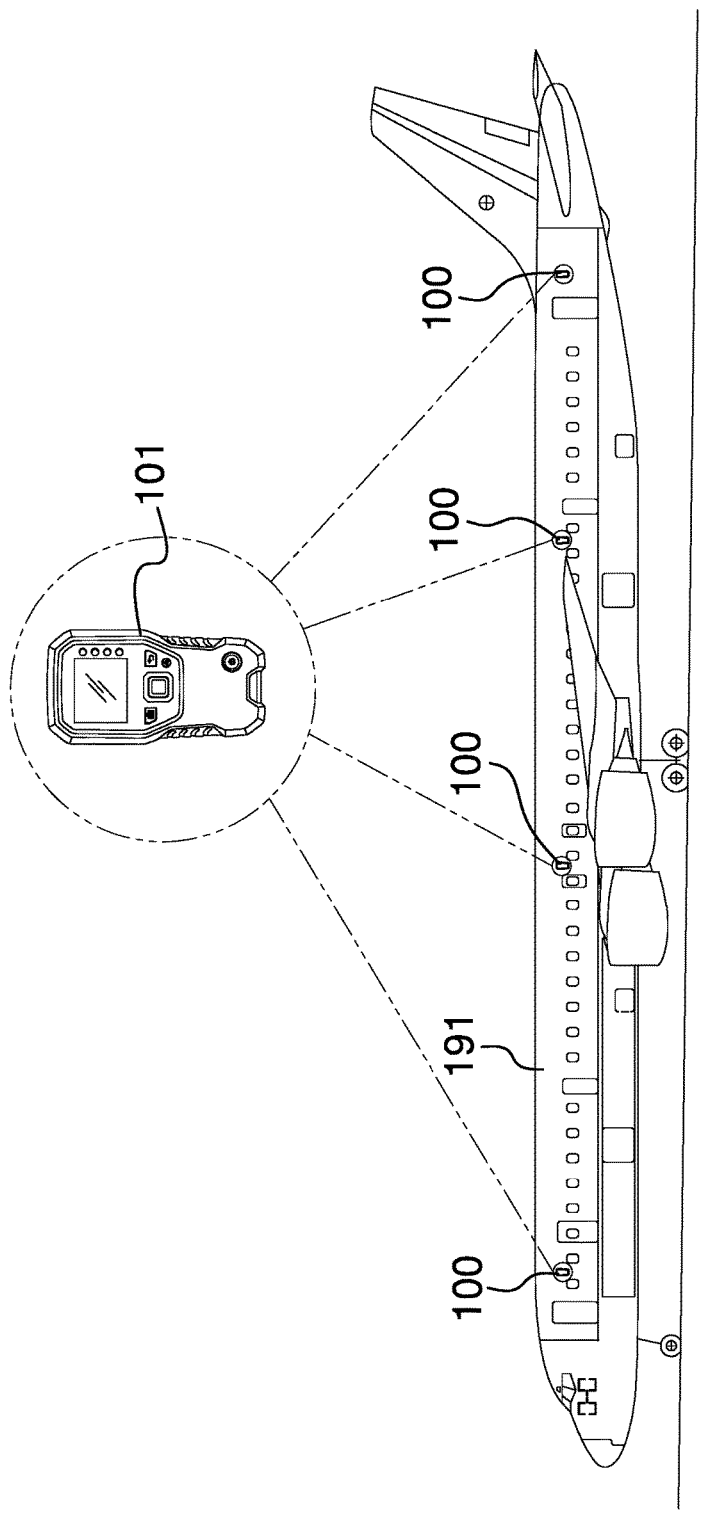
FIG. 6 is an in use view of an embodiment of the disclosure.
Figure 7:
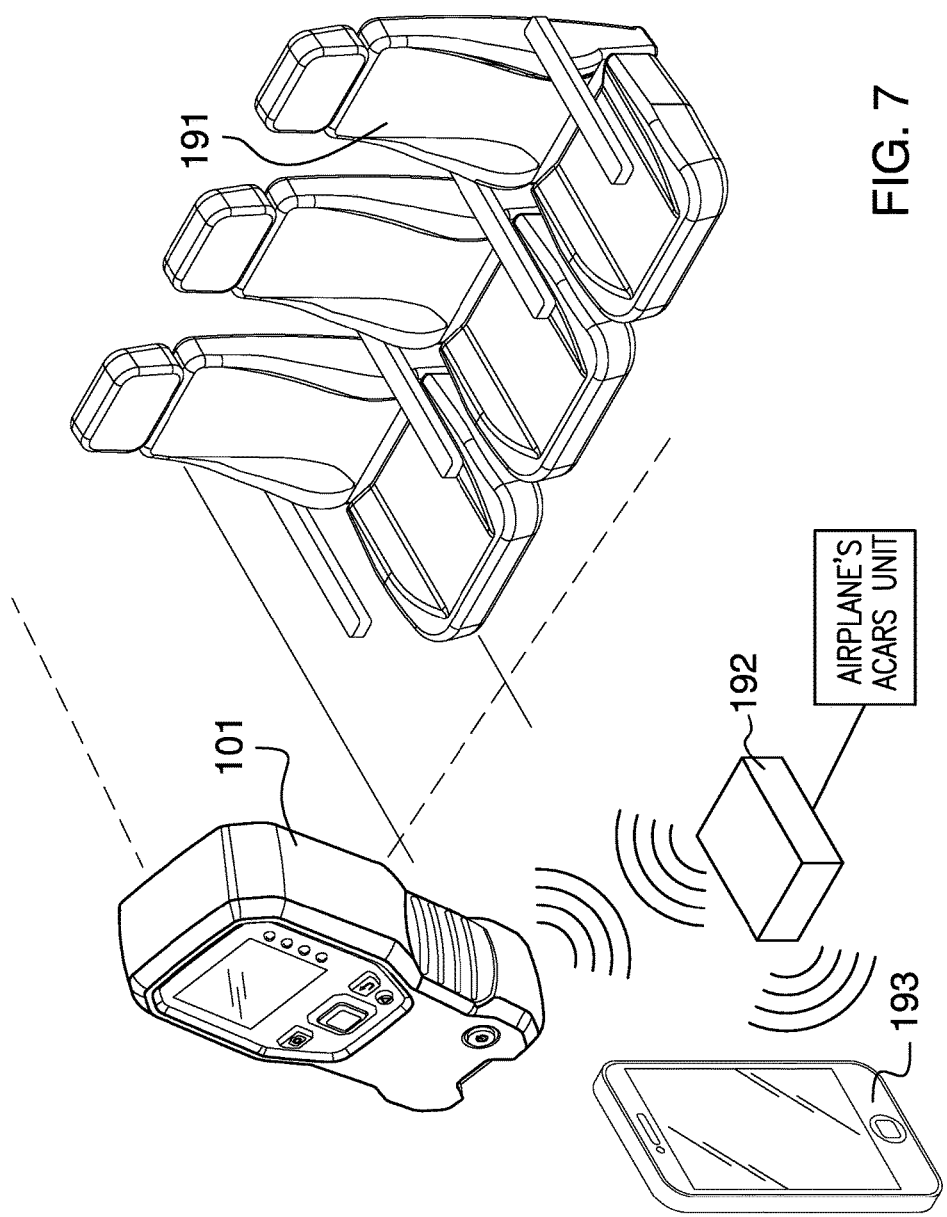
FIG. 7 is an in use view of an embodiment of the disclosure.
Figure 8:
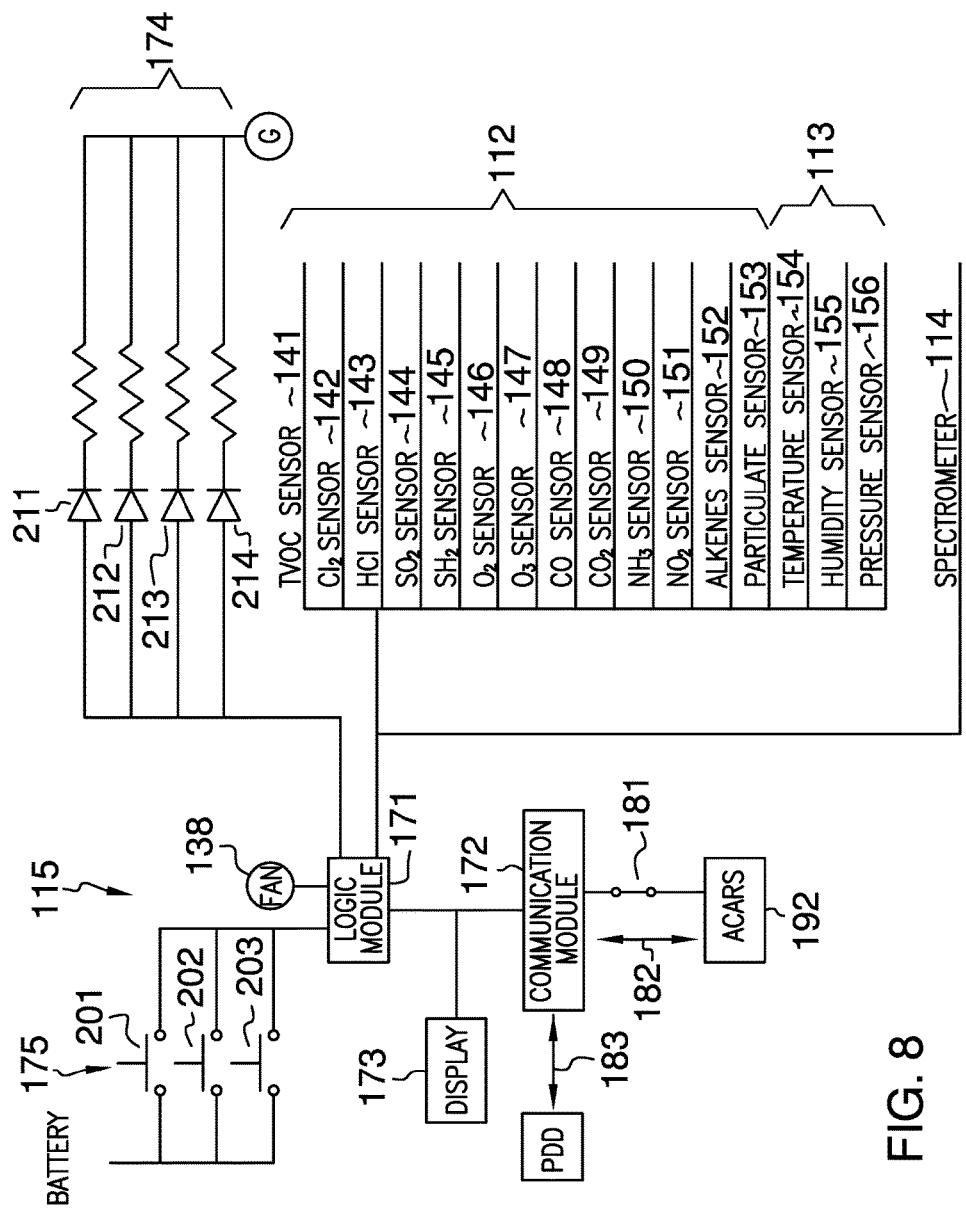
FIG. 8 is a block diagram of an embodiment of the disclosure.
Figure 9:
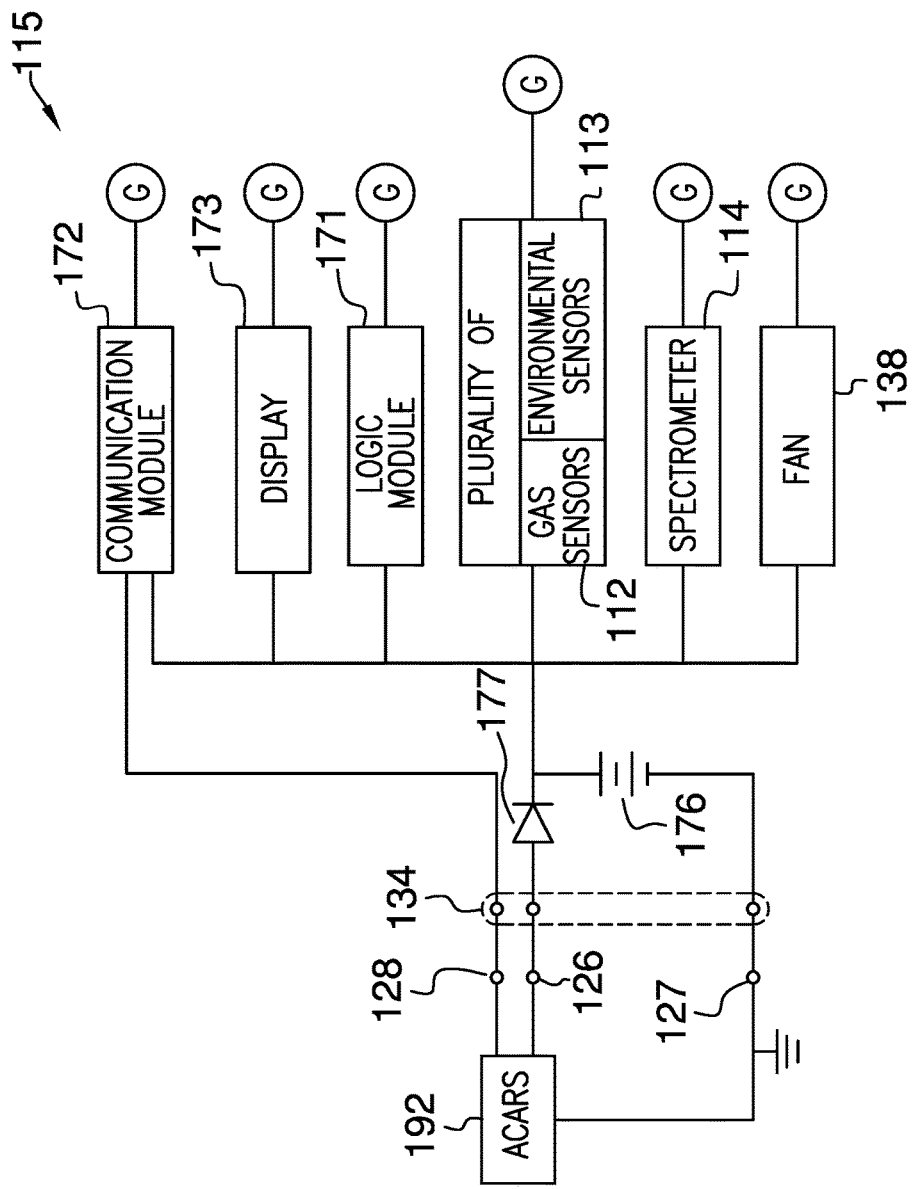
FIG. 9 is a block diagram of an embodiment of the disclosure.
Figure 11:
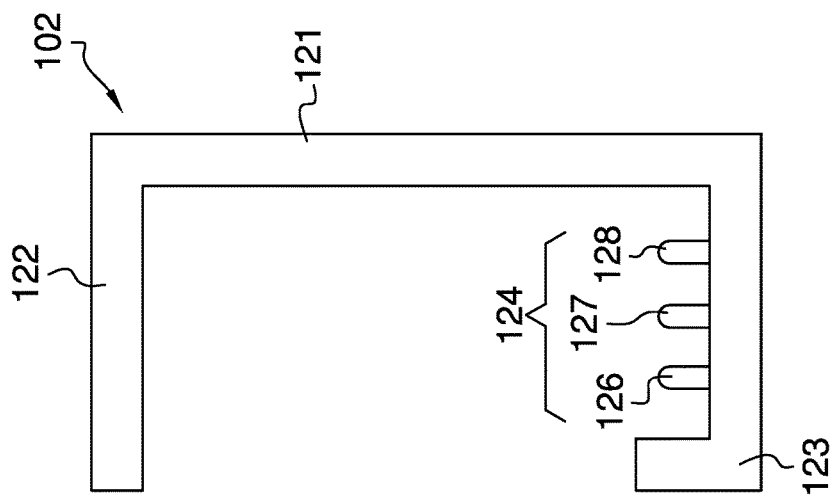
FIG. 11 is a detail view of an embodiment of the disclosure.
Figure 10:
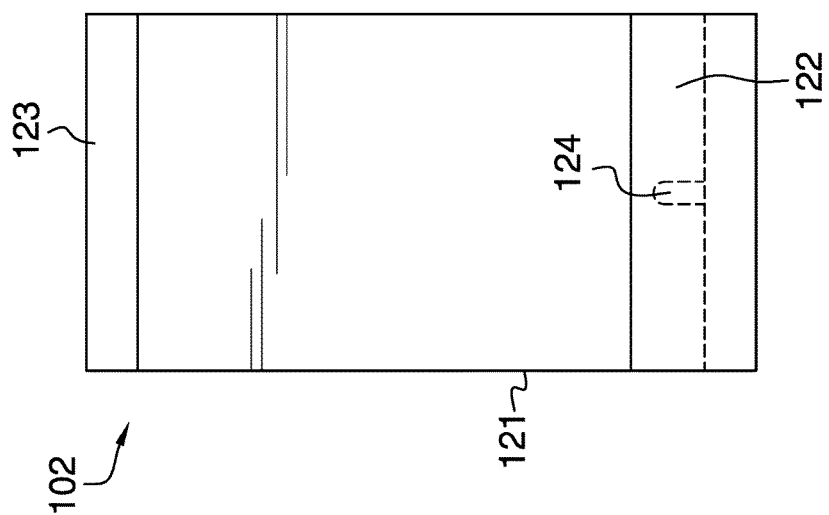
FIG. 10 is a detail view of an embodiment of the disclosure.
Figure 12:
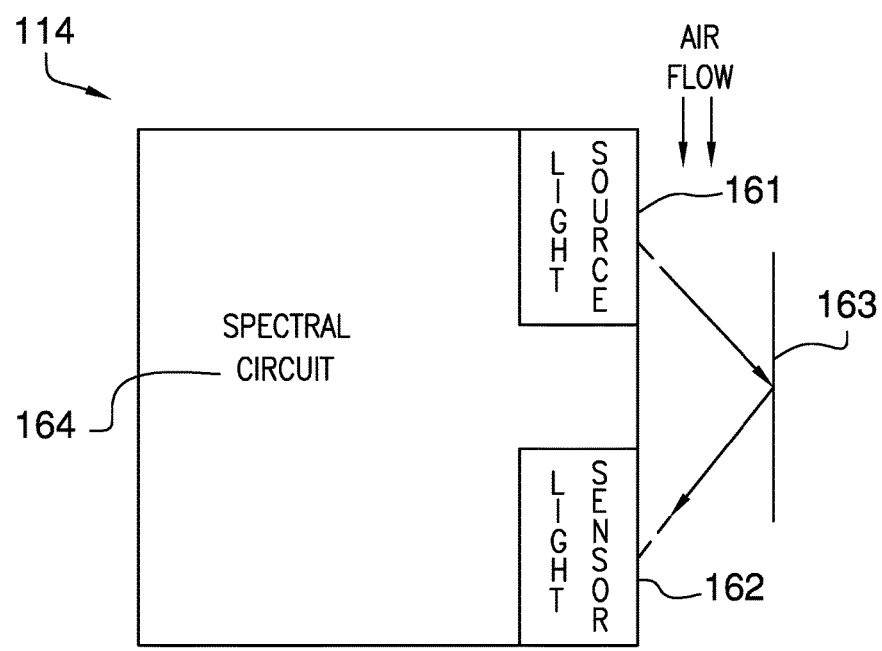
FIG. 12 is a detail view of an embodiment of the disclosure.

Detailed reference will now be made to one or more potential embodiments of the disclosure, which are illustrated in FIGS. 1 through 12.

The airplane cabin air quality monitoring system 100 (hereinafter invention) is a handheld measurement device. The invention 100 is configured for use within an aircraft 191. The invention 100 is an integrated test device that measures the atmosphere within an aircraft 191 for a plurality of potentially hazardous gases and provides immediate results of the measurements to the flight crew. The plurality of potentially hazardous gases comprises one or more chemical substances that are selected such that: 1) the chemical substance will be in a gas phase at normal temperature and pressure conditions; 2) there is a chemical mechanism that causes, or a significant occurrence probability that, the chemical substance can accumulate within the confined space of the aircraft 191; and, 3) the chemical substance is a substance about which health concerns may potentially exist.

The aircraft 191 refers to an aircraft 191 within which the invention 100 is maintained. The ACARS 192 refers to an electronic communication device that is installed in the aircraft 191. The ACARS 192 is discussed in greater detail elsewhere in this disclosure. A personal data device 193 is a personal electronic device that is maintained by an individual associated with the flight crew. The personal data device 193 is discussed in greater detail elsewhere in this disclosure.

The invention 100 comprises a gas monitor 101. The gas monitor 101 tests the atmosphere within an aircraft 191 for the plurality of potentially hazardous gases. The gas monitor 101 further comprises a housing 111, a plurality of gas sensors 112, a plurality of compensation sensors 113, a spectrometer 114, and a control system 115. The plurality of gas sensors 112, the plurality of compensation sensors 113, the spectrometer 114, and the control system 115 are electrically interconnected. The plurality of gas sensors 112, the plurality of compensation sensors 113, the spectrometer 114, and the control system 115 are contained within the housing 111. The control system 115 manages and regulates the operation of the gas monitor 101.

The control system 115 further collects the measurements taken by the plurality of gas sensors 112, the plurality of compensation sensors 113, and the spectrometer 114. Each of the plurality of gas sensors 112 is a commercially available gas sensor that is dedicated to detecting a gas selected from the plurality of potentially hazardous gases. Because the readings of many of the plurality of gas sensors 112 will vary in a known fashion with changes in environmental conditions, the control system 115 uses the data collected from the plurality of compensation sensors 113 to adjust the reported measurements to compensate for these environmental factors. Each of the plurality of compensation sensors 113 comprises a sensor that is dedicated to measuring an environmental condition for this purpose.

The spectrometer 114 is a failsafe mechanism that is incorporated into the gas monitor 101. Specifically, the spectrometer 114 takes spectrometric readings of the atmosphere. The control system 115 then: 1) compares the spectrometric readings with a previously provided standard for atmospheric air to determine if something unidentified is in the atmosphere; 2) generates an alert if something unidentified is detected in the atmosphere; and, 3) stores the spectrometric readings to allow for further analysis at a future date.

The invention 100 further comprises a docking station 102 that stores the gas monitor 101 when the gas monitor 101 is not in use. The docking station 102: 1) recharges the battery 176 of the gas monitor 101; and, 2) establishes a hardwired third communication link 183 between the gas monitor 101 and the ACARS 192 of the aircraft 191

In the first potential embodiment of the disclosure, the plurality of potentially hazardous gases comprises volatile organic compounds, chlorine (CAS 7782-50-5), hydrogen chloride (CAS 7647-01-0), sulfur dioxide (CAS 7446-09-05), hydrogen sulfide (CAS 7783-06-04), oxygen (CAS 7782-44-7), ozone (CAS 10028-15-6), carbon monoxide (CAS 630-08-0), carbon dioxide (CAS 124-38-9), ammonia (CAS 7664-41-7), nitrogen dioxide (CAS 10102-44-0), alkanes, and particulates.

The volatile organic compounds are a potential component of atmospheric gases within an aviation environment. Sources of volatile organic compounds include, but are not limited to, jet fuels, lubricants and hydraulic fluids used in the auxiliary power units, tricresyl phosphate (CAS 1330-78-5) and other lubricants.

The chlorine (CAS 7782-50-5) is a potential component of atmospheric gases within an aviation environment. Sources of chlorine (CAS 7782-50-5) include, but are not limited to, solvents and cleaning fluids.

The hydrogen chloride (CAS 7647-01-0) is a potential component of atmospheric gases within an aviation environment. Sources of hydrogen chloride (CAS 7647-01-0) include, but are not limited to, solvents and cleaning fluids.

The sulfur dioxide (CAS 7446-09-05) is a potential component of atmospheric gases within an aviation environment. Sources of sulfur dioxide (CAS 7446-09-05) include, but are not limited to, the overheating of electronics and wiring systems within the aircraft 191.

The hydrogen sulfide (CAS 7783-06-04) is a potential component of atmospheric gases within an aviation environment. Sources of hydrogen sulfide (CAS 7783-06-04) include, but are not limited to, the overheating of electronics and wiring systems within the aircraft 191.

The oxygen (CAS 7782-44-7) is a significant component of atmospheric gases within an aviation environment.

The ozone (CAS 10028-15-6) is a potential component of atmospheric gases within an aviation environment. Sources of ozone (CAS 10028-15-6) include, but are not limited to, chemical reactions between volatile organic compounds and nitrogen compounds already within the atmosphere.

The carbon monoxide (CAS 630-08-0) is a potential component of atmospheric gases within an aviation environment. Sources of carbon monoxide (CAS 630-08-0) include, but are not limited to, incomplete combustion reactions within the aircraft 191.

The carbon dioxide (CAS 124-38-9) is a potential component of atmospheric gases within an aviation environment. Sources of carbon dioxide (CAS 124-38-9) include, but are not limited to, respiration and combustion activities within the aircraft 191.

The ammonia (CAS 7664-41-7) is a potential component of atmospheric gases within an aviation environment. Sources of ammonia (CAS 7664-41-7) include, but are not limited to, solvents and cleaning fluids.

The nitrogen dioxide (CAS 10102-44-0) is a potential component of atmospheric gases within an aviation environment. Sources of nitrogen dioxide (CAS 10102-44-0) include, but are not limited to, the unavoidable result of secondary reactions related to the primary combustion reactions generated within the engines and auxiliary power units of the aircraft 191.

The alkanes are a potential component of atmospheric gases within an aviation environment. Sources of alkanes include, but are not limited to, jet fuels and other organic combustible products.

The particulates are a potential component of atmospheric gases within an aviation environment. Sources of particulates include, but are not limited to, dirt and debris generally brought into the aircraft 191 by the passengers and flight crew.

The gas monitor 101 is a device that measures a sample of atmospheric gases for the purpose of detecting one or more gases selected from a previously selected plurality of potentially hazardous gases. The previously selected gases included in the plurality of potentially hazardous gases are selected based on: 1) the potential for adverse health effects; and, 2) the probability of being found in the confined space of an aircraft 191. The gas monitor 101 comprises a housing 111, a plurality of gas sensors 112, a plurality of compensation sensors 113, a spectrometer 114, and a control system 115.

The housing 111 is a rectilinear structure. The housing 111 is a casing within which the balance of the gas monitor 101 is contained. The housing 111 is formed with all apertures and form factors necessary to allow the housing 111 to accommodate the functions of the gas monitor 101. The housing 111 comprises a shell 131, a control chamber 132, a flow chamber 133, a port 134, a grip 135, and a copper foil 139.

The shell 131 is a rigid rectilinear structure that forms the exterior surface of the housing 111. The copper foil 139 is a readily and commercially available flexible sheeting formed from copper. The copper foil 139 is used to line the interior surfaces of the shell 131 for the purpose of inhibiting electromagnetic interference that may be generated by the invention 100. The control chamber 132 is a segregated chamber formed within the shell 131. The control chamber 132 is used to house the control system 115. The port 134 is an electrical connection that receives the plug 124 of the docking station 102. The port 134 transfers electrical power and communication signals between the control system 115 and the ACARS 192. The grip 135 is an accommodation that is formed in the shell 131 for the purpose of holding and handling the gas monitor 101.

The flow chamber 133 is a segregated chamber formed within the shell 131. The flow chamber 133 contains the plurality of gas sensors 112, the plurality of compensation sensors 113, and the spectrometer 114. During the operation of the invention 100, gases from the atmosphere are forced through the flow chamber 133 to provide the gas samples required by the plurality of gas sensors 112, the plurality of compensation sensors 113, and the spectrometer 114 for the purpose of taking measurements. The flow chamber 133 comprises an intake vent 136, an exhaust vent 137, and a fan 138.

The intake vent 136 is an aperture formed through the shell 131 for the purpose of drawing atmospheric gases into the flow chamber 133. The exhaust vent 137 is an aperture formed through the shell 131 for the purpose of expelling atmospheric gases from the flow chamber 133. The fan 138 is an electrically powered mechanical device that pumps atmospheric gases through the flow chamber 133. The fan 138 is mounted in the intake vent 136.

Each of the plurality of gas sensors 112 is an electrically operated sensor that is used to detect a gas selected from the plurality of potentially hazardous gases. The plurality of gas sensors 112 comprises a TVOC sensor 141, a chlorine sensor 142, a hydrogen chloride sensor 143, a sulfur dioxide sensor 144, a hydrogen sulfide sensor 145, an oxygen sensor 146, an ozone sensor 147, a carbon monoxide sensor 148, a carbon dioxide sensor 149, an ammonia sensor 150, a nitrogen dioxide sensor 151, an alkanes sensor 152, and a particulates sensor 153.

The TVOC sensor 141 measures the concentration of total volatile organic compounds in the atmosphere. The TVOC sensor 141 monitors the atmosphere for total volatile organic compounds using a CCS811 sensor sourced from AMS. The footprint of the CCS811 is approximately 5 mm×5 mm (0.2 in×0.2 in).

The chlorine sensor 142 measures the concentration of diatomic chlorine (CAS 7782-50-5) in the atmosphere. The chlorine sensor 142 monitors the atmosphere for chlorine (CAS 7782-50-5) using an ME3-CL2 sensor sourced from Winsen Sensors. The footprint of the ME3-CL2 is approximately 16 mm×20 mm (0.6 in ×0.8 in).

The hydrogen chloride sensor 143 measures the concentration of hydrogen chloride (CAS 7647-01-0) in the atmosphere. The hydrogen chloride sensor 143 monitors the atmosphere for hydrogen chloride (CAS 7647-01-0) using an ME3-HCl sensor sourced from Winsen Sensors. The footprint of the ME3-HCl is approximately 16 mm×20 mm (0.6 in×0.8 in).

The sulfur dioxide sensor 144 measures the concentration of sulfur dioxide (CAS 7446-09-05) in the atmosphere. The sulfur dioxide sensor 144 monitors the atmosphere for sulfur dioxide (CAS 7446-09-05) using an ME3-SO2 sensor sourced from Winsen Sensors. The footprint of the ME3-SO2 is approximately 16 mm×20 mm (0.6 in×0.8 in).

The hydrogen sulfide sensor 145 measures the concentration of hydrogen sulfide (CAS 7783-06-04) in the atmosphere. The hydrogen sulfide sensor 145 monitors the atmosphere for hydrogen sulfide (CAS 7783-06-04) using an ME3-SH2 sensor sourced from Winsen Sensors. The footprint of the ME3-SH2 is approximately 16 mm×20 mm (0.6 in×0.8 in).

The oxygen sensor 146 measures the concentration of diatomic oxygen (CAS 7782-44-7) in the atmosphere. The oxygen sensor 146 monitors the atmosphere for oxygen (CAS 7782-44-7) using an ME3-O2 sensor sourced from Winsen Sensors. The footprint of the ME3-O2 is approximately 16 mm×20 mm (0.6 in×0.8 in).

The ozone sensor 147 measures the concentration of ozone (CAS 10028-15-6) in the atmosphere. The ozone sensor 147 monitors the atmosphere for ozone (CAS 10028-15-6) using an ME3-sensor sourced from Winsen Sensors. The footprint of the ME3-O3 is approximately 16 mm×20 mm (0.6 in×0.8 in).

The carbon monoxide sensor 148 measures the concentration of carbon monoxide (CAS 630-08-0) in the atmosphere. The carbon monoxide sensor 148 monitors the atmosphere for carbon monoxide (CAS 630-08-0) using an ME3-CO sensor sourced from Winsen Sensors. The footprint of the ME3-CO is approximately 16 mm×20 mm (0.6 in×0.8 in).

The carbon dioxide sensor 149 measures the concentration of carbon dioxide (CAS 124-38-9) in the atmosphere. The carbon dioxide sensor 149 monitors the atmosphere for carbon dioxide (CAS 124-38-9) using the CCS811 sensor sourced from AMS. The footprint of the CCS811 is approximately 5 mm×5 mm (0.2 in×0.2 in).

The ammonia sensor 150 measures the concentration of ammonia (CAS 7664-41-7) in the atmosphere. The ammonia sensor 150 monitors the atmosphere for ammonia (CAS 7664-41-7) using an ME3-NH3 sensor sourced from Winsen Sensors. The footprint of the ME3-NH3 is approximately 16 mm×20 mm (0.6 in×0.8 in).

The nitrogen dioxide sensor 151 measures the concentration of nitrogen dioxide (CAS 10102-44-0) in the atmosphere. The nitrogen dioxide sensor 151 monitors the atmosphere for nitrogen dioxide (CAS 10102-44-0) using an ME3-NO2 sensor sourced from Winsen Sensors. The footprint of the ME3-NO2 is approximately 16 mm×20 mm (0.6 in×0.8 in).

The alkanes sensor 152 is a combustibles sensor that primarily measures the concentration of alkanes in the atmosphere. The alkanes sensor 152 monitors the atmosphere for alkanes using an MC113 sensor sourced from Winsen Sensors. The footprint of the MC113 is approximately 16 mm×20 mm (0.6 in×0.8 in).

The particulates sensor 153 measures the concentration of particulates in the atmosphere. The particulates sensor 153 monitors the atmosphere for particulates using a ZH03A sensor sourced from Winsen Sensors. The footprint of the ZH03A is approximately 30 mm×50 mm (1.2 in ×1.9 in).

Each of the plurality of compensation sensors 113 is a sensor that is used to measure environmental conditions of the tested atmosphere. The readings collected from the plurality of compensation sensors 113 are used to adjust the measurements taken by each of the plurality of gas sensors 112 to compensate for known measurement variations created by environmental conditions. The plurality of compensation sensors 113 comprises a temperature sensor 154, a humidity sensor 155, and a pressure sensor 156.

The temperature sensor 154 measures the temperature of the atmosphere. The temperature sensor 154 measures the temperature of the atmosphere using a SHT1X sensor sourced from Sensirion. The footprint of the SHT1X is approximately 5 mm×7 mm (0.2 in×0.3 in). The humidity sensor 155 measures the humidity of the atmosphere. The humidity sensor 155 measures the humidity of the atmosphere using the SHT1X sensor sourced from Sensirion. The footprint of the SHT1X is approximately 5 mm×7 mm (0.2 in×0.3 in). The pressure sensor 156 measures the pressure of the atmosphere. The pressure sensor 156 measures the pressure of the atmosphere using a BMP180 sensor sourced from Bosch. The footprint of the BMP180 is approximately 5 mm×5 mm (0.2 in×0.2 in).

Methods to adjust sensor readings collected from the plurality of gas sensors 112 to compensate for variations in temperature, humidity and pressure are known and documented by the vendors of each of the plurality of gas sensors 112.

The spectrometer 114 is an electrical device that performs a spectral analysis of the atmospheric sample. The spectrometer reflects one or more beams of electromagnetic radiation of known frequencies through the atmospheric sample and measures the spectrum of the returned beam. The spectrometer 114 transmits the measured spectrum of the returned beam to a logic module 171 within the control system 115 for analysis. The logic module 171 performs a spectral analysis on the return beam data to determine if any unexpected spectral absorptions are detected. If unexpected spectral absorptions are detected, this would indicate the presence of an unidentified chemical substance in the atmosphere. In this circumstance, the logic module 171: 1) stores the spectral measurements for future analysis by more specialized equipment; and, 2) generates an alert to the flight crew. The spectrometer 114 comprises a light source 161, a light sensor 162, a reflective surface 163, and a spectral circuit 164.

The light source 161 comprises one or more LEDs that are incorporated into the spectrometer 114. The light source 161 is calibrated to emit electromagnetic radiation at one or more previously determined wavelengths.

The light sensor 162 is a sensor that is calibrated to detect electromagnetic radiation over a range of previously determined frequencies. The light sensor 162 is incorporated into the spectrometer 114. The light sensor 162 receives the electromagnetic radiation generated by the light source 161 after the electromagnetic radiation has passed through the atmospheric gas sample.

The reflective surface 163 is a mirrored structure that reflects the light generated by the light source 161 to the light sensor 162 as the generated light is passing through the atmospheric gases.

The spectral circuit 164 is an electrical circuit incorporated into the spectrometer 114 for the purpose of subdividing the received light into spectral ranges for analysis by the logic module 171.

The spectrometer 114 performs the spectral analysis on the atmospheric gases using an AS7263 spectrometric device sourced from AMS. The footprint of the spectrometer 114 is approximately 5 mm×5 mm (0.2 in×0.2 in).

The control system 115 is a programmable electrical device that manages and regulates the operation of the invention 100. The control system 115 comprises a logic module 171, a communication module 172, a display 173, a plurality of LEDs 174, a plurality of switches 175, a battery 176 and a diode 177.

The logic module 171 is a readily and commercially available programmable electronic device that is used to manage, regulate, and operate the control system 115. Depending on the specific design and the selected components, the logic module 171 can be a separate component within the control system 115 or the functions of the logic module 171 can be incorporated into another component within the control system 115.

The logic module 171: 1) monitors each of the plurality of gas sensors 112; 2) monitors each of the plurality of compensation sensors 113; 3) calculates the compensated concentration of each of the plurality of potentially hazardous gases based on the readings from both the plurality of gas sensors 112 and the plurality of compensation sensors 113; 4) compares the compensated concentrations of each of the plurality of potentially hazardous gases against a predetermined exposure level; 5) displays the calculated compensated concentration levels for each of the plurality of potentially hazardous gases on the display 173; 6) generates an alert using the plurality of LEDs 174 should a gas selected from the plurality of potentially hazardous gases exceed a predetermined exposure limit; 7) transmits the calculated compensation concentrations to the ACARS 192; and, 8) monitors the plurality of switches 175 to receive operating instructions from the flight crew.

The communication module 172 is a wireless electronic communication device that allows the logic module 171 to wirelessly communicate with a locally presented device such as a personal data device 193 using a third communication link 183. The communication module 172 further establishes a wireless second communication link 182 in order to transmit data collected from the plurality of gas sensors 112 to the ACARS 192. In the first potential embodiment of the disclosure the communication module 172 further supports a hardwired first communication link 181 with the ACARS 192 that is provisioned through the plug 124 of the docking station 102. The communication module 172 supports one or more wireless communication protocols selected from the group consisting of a WiFi protocol or a Bluetooth protocol.

Specifically, in the first potential embodiment of the disclosure, the first communication link 181 is a hardwired communication link between the communication module 172 and the ACARS 192. The second communication link 182 is a wireless communication link that is established between the communication module 172 and the ACARS 192. The third communication link 183 is a wireless communication link that is established between the communication module 172 and a personal data device 193.

The display 173 is a commercially available LCD that the logic module 171 uses to display the calculated compensated concentrations of each of the monitored gases to the flight crew.

The battery 176 is a commercially available rechargeable battery 176. The chemical energy stored within the battery 176 is renewed and restored through use of the port 134. The port 134 is an electrical circuit that reverses the polarity of the battery 176 and provides the energy necessary to reverse the chemical processes that the battery 176 initially used to generate the electrical energy. This reversal of the chemical process creates a chemical potential energy that will later be used to generate electricity. The port 134 attaches to the ACARS 192 from which it draws electrical energy. The diode 177 is an electrical device that allow electric current to flow in only one direction. The diode 177 is installed between the battery 176 and the port 134 such that electricity will not flow from the positive terminal of the battery 176 to the positive terminal 126 of the plug 124.

Each of the plurality of LEDs 174 is an electrical device that is illuminated by the logic module 171 to indicate an operating condition or alert. The plurality of LEDs 174 comprises a first LED 211, a second LED 212, a third LED 213, and a fourth LED 214. The first LED 211 is a readily and commercially available LED. The first LED 211 is used to indicate that the gas monitor 101 is available for operation. The second LED 212 is a readily and commercially available LED. The second LED 212 is used to indicate that the testing procedures are in process. The third LED 213 is a readily and commercially available LED. The third LED 213 is used to indicate that the logic module 171 has generated an alert. The fourth LED 214 is a readily and commercially available LED. The fourth LED 214 is used to indicate that the logic module 171 has generated an alert that requires immediate attention from the flight crew.

Each of the plurality of switches 175 is an electrical device that is used by the flight crew to provide operational instruction to the logic module 171. The plurality of switches 175 comprises a first switch 201, a second switch 202, and a third switch 203. The first switch 201 is a readily and commercially available momentary switch. The first switch 201 is used to instruct the logic module 171 to initiate operation. The second switch 202 is a readily and commercially available momentary switch. The second switch 202 is used to instruct the logic module 171 to initiate testing operations. The third switch 203 is a readily and commercially available momentary switch. The third switch 203 is used to instruct the logic module 171 to transmit the calculated compensated concentrations, spectral analysis data, and any alerts to the ACARS 192 and the personal data device 193.

The docking station 102 is a rectilinear structure that: 1) stores the gas monitor 101 when not in use; 2) recharges the battery 176 during storage of the gas monitor 101; and, 3) provides a hardwired electrical connection called the first communication link 181 between the gas monitor 101 and the ACARS 192 unit of the aircraft 191. The docking station 102 comprises a stanchion 121, a base 122, a cap 123, and a plug 124.

The stanchion 121 is a rectangular plate that attaches the base 122 to the cap 123. The stanchion 121 is directly and permanently attached to a bulkhead within the aircraft 191. The base 122 is a horizontal surface which: 1) vertically supports the gas monitor 101 within the docking station 102; and, 2) contains the plug 124 which is inserted into the port 134 of the gas monitor 101. The base 122 projects perpendicularly away from the stanchion 121. The cap 123 is a horizontal surface that projects perpendicularly away from the stanchion 121. The cap 123 projects in the same direction as the base 122. The cap 123 attaches to the end of the stanchion 121 that is distal from the base 122. The purpose of the cap 123 is to contain the gas monitor 101 within the docking station 102 during turbulence.

The plug 124 is an electrical termination that is matched to the port 134 of the gas monitor 101. The plug 124 electrically connects the gas monitor 101 to the ACARS 192 such that electrical power and data may be exchanged between the gas monitor 101 and the ACARS 192. The plug 124 comprises a positive terminal 126, a negative terminal 127, and a communication terminal 128.

The positive terminal 126 is an electrical termination that electrically connects the plug 124 to the positive terminal of the battery 176 through the diode 177. The negative terminal 127 is an electrical termination that electrically connects the plug 124 to the negative terminal of the battery 176. The communication terminal 128 is an electrical termination that electrically connects the plug 124 to the first communication link 181 of the communication module 172.

To use the invention 100, the gas monitor 101 is removed from the docking station 102 and brought to the location within the aircraft 191 to be tested. The first switch 201 is actuated to turn the invention 100 on. The second switch 202 is then actuated to initiate the atmospheric testing. The logic module 171 turns on the fan 138 to force atmospheric gases through the flow chamber 133. The logic module 171 then collects the appropriate data from the plurality of gas sensors 112, the plurality of compensation sensors 113, and the spectrometer 114. The logic module 171 then calculates the calculated compensated concentration level for each of the plurality of potentially hazardous gases and displays the calculated compensated concentration levels on the display 173. The logic module 171 further analyzes the spectral measurements from the spectrometer 114. Based on the calculated compensated concentration levels and the spectral measurements analysis, the logic module 171 will also activate the plurality of LEDs 174 as required and send reports to the ACARS 192 as required.

The following definitions were used in this disclosure:

ACARS: As used in this disclosure, ACARS is an abbreviation for the Aircraft Communication and Reporting System. The ACARS is an automated flight data communication system that transmits flight management and aircraft maintenance information between an operating aircraft and a ground station acting as an appropriate authority.

Alkane: As used in this disclosure, an alkane refers to molecule formed from a carbon chain wherein all carbon-to-carbon bonds within the molecule are single bonds. An alkane is often referred to as a saturated hydrocarbon.

Ammonia: As used in this disclosure, ammonia (CAS 7664-41-7) refers to a chemical compound with the formula HN3. The chemical term ammonium (CAS 14789-03-9) refers to an ammonia molecule that has formed a hydrogen bond with a hydrogen ion. Ammonium has the chemical formula NH4+. The chemical quaternary ammonium (CAS 8001-54-5) refers to a chemical compound wherein the hydrogen elements of ammonium, including the hydrogen-bonded hydrogen ion are replaced with other molecules or atoms (potentially including hydrogen).

Appropriate Authority: As used in this disclosure, an appropriate authority is a previously determined person or organization that is designated to receive alarm or other notification messages regarding a monitored system or activity.

Battery: As used in this disclosure, a battery is a chemical device consisting of one or more cells, in which chemical energy is converted into electricity and used as a source of power.

Bluetooth: As used in this disclosure, Bluetooth is a standardized communication protocol that is used to wirelessly interconnect electronic devices.

Bulkhead: As used in this disclosure, a bulkhead is a vertical barrier, often referred to as a wall, which subdivides a space into compartments.

Cable: As used in this disclosure, a cable is a collection of insulated wires covered by a protective casing that is used for transmitting electricity or telecommunication signals.

Carbon Monoxide: As used in this disclosure, carbon monoxide (CAS 630-08-0) refers to a chemical compound with the formula CO.

Carbon Dioxide: As used in this disclosure, carbon dioxide (CAS 124-38-9) refers to a chemical compound with the formula CO2.

Chlorine: As used in this disclosure, chlorine (CAS 7782-50-5) refers to the element with atomic number 22 in the periodic table. The standard abbreviation for chlorine is Cl. Chlorine is a diatomic element and can also be abbreviated as Cl2.

Control System: As used in this disclosure, a control system is a first device or system that manages and regulates the behavior or operation of a second device or system.

Diode: As used in this disclosure, a diode is a two terminal semiconductor device that allows current flow in only one direction. The two terminals are called the anode and the cathode. Electric current is allowed to pass from the anode to the cathode.

Display: As used in this disclosure, a display is a surface upon which is presented an image, potentially including, but not limited to, graphic images and text, that is interpretable by an individual viewing the projected image in a meaningful manner.

Electrical Ground: As used in this disclosure, an electrical ground is a common reference voltage that is used in the design and implementation of electrical circuits. An electrical ground is often, but not necessarily, the discharge point of electric currents flowing through an electric circuit.

Evaporation: As used in this disclosure, evaporation refers to a phase transition from a liquid phase to a gas.

Fan: As used in this disclosure, a fan is a mechanical device with rotating blades that is used to create a flow or current of air.

Footprint: As used in this disclosure, a footprint is the surface area occupied by an object.

Form Factor: As used in this disclosure, the term form factor refers to the size and shape of an object.

Grip: As used in this disclosure, a grip is an accommodation formed within an object that allows the object to be grasped or manipulated by a hand.

Hardwired: As used in this disclosure, the term hardwired refers to a physical electrical connection, generally using cable, between two electrical circuits or circuit elements. Such a hardwired connection is considered more reliable than a wireless connection.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Housing: As used in this disclosure, a housing is a rigid casing that encloses and protects one or more devices.

Hydrochloric Acid: As used in this disclosure, hydrochloric acid (CAS 7647-01-0) is an ionically bound molecule comprising hydrogen and chlorine with the molecular formula HCl. Hydrochloric acid is also known as hydrogen chloride.

Hydrogen Sulfide: As used in this disclosure, hydrogen sulfide (CAS 7783-06-04) refers to a chemical compound with the formula H2S.

LCD: As used in this disclosure, LCD is an acronym for Liquid Crystal Display. A liquid crystal display comprises a liquid crystal film placed between two sheets of transparent material. The visual characteristics of the LCD can be varied through the application of a voltage.

LED: As used in this disclosure, an LED is an acronym for a light emitting diode. A light emitting diode is a diode that is also a light source.

Limit Resistor: As used in this disclosure, a limit resistor is an electrical resistor that is used to limit the flow of electric current through an electrical circuit.

Logic Module: As used in this disclosure, a logic module is a readily and commercially available electrical device that is programmable and that accepts digital and analog inputs, processes the digital and analog inputs according to previously stored instruction and provides the results of these instructions as digital or analog outputs.

Momentary Switch: As used in this disclosure, a momentary switch is a biased switch in the sense that the momentary switch has a baseline position that only changes when the momentary switch is actuated (for example when a pushbutton switch is pushed). The momentary switch then returns to the baseline position once the actuation is completed. This baseline position is called the "normal" position. For example, a "normally open" momentary switch interrupts (open) the electric circuit in the baseline position and completes (closes) the circuit when the momentary switch is activated. Similarly, a "normally closed" momentary switch will complete (close) an electric circuit in the baseline position and interrupt (open) the circuit when the momentary switch is activated.

Nitrogen: As used in this disclosure, nitrogen (CAS 7727-37-9) refers to the element with atomic number 7 in the periodic table. The chemical abbreviation for nitrogen is N2.

Nitrogen Dioxide: As used in this disclosure, nitrogen dioxide (CAS 10102-44-0) refers to a chemical compound with the formula NO2.

Normal Temperature and Pressure: As used in this disclosure, normal temperature and pressure refers to atmospheric conditions corresponding to 20 degrees C. at 100 kPa (or approx. 1 atmosphere). Normal temperature and pressure is often abbreviated as NTP.

Oxygen: As used in this disclosure, oxygen (CAS 7782-44-7) refers to the element with atomic number 8 in the periodic table. The chemical abbreviation for oxygen is O2.

Ozone: As used in this disclosure, ozone (CAS 10028-15-6) refers to a chemical compound with the formula O3.

PDD: As used in this disclosure, PDD is an acronym for personal data device.

Personal Data Device: As used in this disclosure, a personal data device is a handheld device that is used for managing personal information and communication. Examples of personal data device include, but are not limited to, cellular phones, tablets and smart phones.

Plug: As used in this disclosure, a plug is an electrical termination that electrically connects a first electrical circuit to a second electrical circuit or a source of electricity.

Port: As used in this disclosure, a port is an electrical termination that is used to connect a first electrical circuit to a second external electrical circuit. In this disclosure, the port is designed to receive a plug.

Rectilinear: As used in this disclosure, rectilinear is an adjective that is used to describe an object that: 1) moves in a straight line or lines; 2) consists of a straight line or lines; 3) is bounded by a straight line or lines; or, 4) is otherwise characterized by a straight line or lines.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Stanchion: As used in this disclosure, a stanchion refers to a vertical support.

Sublimation: As used in this disclosure, sublimation refers to a phase transition directly from a solid phase to a gas phase in a manner that bypasses the liquid phase.

Sulfur Dioxide: As used in this disclosure, sulfur dioxide (CAS 7446-09-05) refers to a chemical compound with the formula SO2.

Switch: As used in this disclosure, a switch is an electrical device that starts and stops the flow of electricity through an electric circuit by completing or interrupting an electric circuit. The act of completing or breaking the electrical circuit is called actuation. Completing or interrupting an electric circuit with a switch is often referred to as closing or opening a switch respectively. Completing or interrupting an electric circuit is also often referred to as making or breaking the circuit respectively.

Terminal: As used in this disclosure, a terminal is the end point of a conductor. A terminal can be the conducting wire itself or may have attached to is a device designed to facilitate an electrical connection.

Tricresyl Phosphate: As used in this disclosure, tricresyl phosphate (CAS 1330-78-5) refers to a chemical compound with the formula C21H21O4P. Tricresyl phosphate has multiple industrial uses including, but not limited to, an additive to enhance fire retardance, hydraulic fluid, heat exchange fluid, and a fuel and lubricant additive. Tricresyl phosphate remains liquid over a wide temperature range (melting point −40 C to boiling point 200 C) which makes it a common choice in situations where a broad range of environmental conditions are anticipated.

Vent: As used in this disclosure, a vent is an opening in the ductwork that allows for the passage of air.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

Volatile: As used in this disclosure, volatile refers to a substance that will evaporate or sublimate into a gas state at room temperatures and pressures.

Volatile Organic Compounds: As used in this disclosure, a volatile organic compounds refers to an organic compounds with a relatively low boiling point such that a significant portion of the volatile organic compounds will exist as a gas at normal temperature and pressure. Volatile organic compounds is commonly abbreviated VOC. When measuring volatile organic compounds within the atmosphere, commercially available sensors will generally measure and report all volatile organic compounds as a single aggregated measurement referred to as the total volatile organic compounds. Total volatile organic compounds is commonly abbreviated TVOC.

WiFi: As used in this disclosure, WiFi refers to the physical implementation of a collection of wireless electronic communication standards commonly referred to as IEEE 802.11x.

Wireless: As used in this disclosure, wireless is an adjective that is used to describe a communication channel between two terminals that does not require the use of physical cabling.

With respect to the above description, it is to be realized that the optimum dimensional relationship for the various components of the invention described above and in FIGS. 1 through 12 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An instrument comprising:
a gas monitor and a docking station;
wherein the docking station stores the gas monitor;
wherein the instrument is a handheld measurement device;
wherein the instrument is configured for use within an aircraft;
wherein the aircraft is further defined with an ACARS and a bulkhead;
wherein the instrument is an integrated test device that measures the atmosphere within the aircraft for a plurality of potentially hazardous gases;
wherein the instrument provides the results of the measurements to a flight crew;
wherein the plurality of potentially hazardous gases comprises one or more chemical substances that are selected from the group consisting of chemical substances that are in a gas phase at normal temperature and pressure conditions;
wherein the gas monitor tests the atmosphere within an aircraft for the plurality of potentially hazardous gases;
wherein the gas monitor further comprises a housing, a plurality of gas sensors, a plurality of compensation sensors, a spectrometer, and a control system;
wherein the plurality of gas sensors, the plurality of compensation sensors, the spectrometer, and the control system are electrically interconnected;
wherein the plurality of gas sensors, the plurality of compensation sensors, the spectrometer, and the control system are contained within the housing;
wherein the control system manages and regulates the operation of the gas monitor;
wherein the control system further collects the measurements taken by the plurality of gas sensors, the plurality of compensation sensors, and the spectrometer;
wherein each of the plurality of gas sensors detects a gas selected from the plurality of potentially hazardous gases;
wherein each of the plurality of compensation sensors measures an environmental condition;
wherein the spectrometer takes spectrometric readings of the atmosphere;
wherein the control system generates an alert if an anomaly is detected in the atmosphere;
wherein the control system stores the spectrometric readings;
wherein the housing is a rectilinear structure;
wherein the housing is a rigid casing within which the balance of the gas monitor is contained;
wherein the housing comprises a shell, a control chamber, a flow chamber, a port, a grip, and a copper foil;
wherein the control chamber, the flow chamber, the port, the grip and the copper foil are contained within the shell;
wherein the control chamber is a segregated chamber formed within the shell;
wherein the control chamber contains the control system;
wherein the port is an electrical connection;
wherein the port transfers electrical power and communication signals between the control system and the ACARS;
wherein the grip is formed in the shell.

2. The instrument according to claim 1
wherein the shell is a rectilinear structure that forms the exterior surface of the housing;
wherein the copper foil is a flexible sheeting formed from copper;
wherein the copper foil lines the interior surfaces of the shell.

3. The instrument according to claim 2
wherein the flow chamber is a segregated chamber formed within the shell;
wherein the flow chamber contains the plurality of gas sensors, the plurality of compensation sensors, and the spectrometer;
wherein during the operation of the instrument gases from the atmosphere are forced through the flow chamber;
wherein the forced air flow provides the gas samples required by the plurality of gas sensors, the plurality of compensation sensors, and the spectrometer.

4. The instrument according to claim 3
wherein the flow chamber comprises an intake vent, an exhaust vent, and a fan;
wherein the intake vent is an aperture formed through the shell;
wherein the exhaust vent is an aperture formed through the shell;
wherein the fan is an electrically powered mechanical device that pumps atmospheric gases through the flow chamber;
wherein the fan is controlled by the control system;
wherein the fan is mounted in the intake vent.

5. The instrument according to claim 4
wherein the plurality of potentially hazardous gases comprises volatile organic compounds, chlorine (CAS 7782-50-5), hydrogen chloride (CAS 7647-01-0), sulfur dioxide (CAS 7446-09-05), hydrogen sulfide (CAS 7783-06-04), oxygen (CAS 7782-44-7), ozone (CAS 10028-15-6), carbon monoxide (CAS 630-08-0), carbon dioxide (CAS 124-38-9), ammonia (CAS 7664-41-7), nitrogen dioxide (CAS 10102-44-0), alkanes, and particulates;

wherein the plurality of gas sensors comprises a TVOC sensor, a chlorine sensor, a hydrogen chloride sensor, a sulfur dioxide sensor, a hydrogen sulfide sensor, an oxygen sensor, an ozone sensor, a carbon monoxide sensor, a carbon dioxide sensor, an ammonia sensor, a nitrogen dioxide sensor, an alkanes sensor, and a particulates sensor;

wherein the TVOC sensor measures the concentration of total volatile organic compounds in the atmosphere;

wherein the chlorine sensor measures the concentration of diatomic chlorine (CAS 7782-50-5) in the atmosphere;

wherein the hydrogen chloride sensor measures the concentration of hydrogen chloride (CAS 7647-01-0) in the atmosphere;

wherein the sulfur dioxide sensor measures the concentration of sulfur dioxide (CAS 7446-09-05) in the atmosphere;

wherein the hydrogen sulfide sensor measures the concentration of hydrogen sulfide (CAS 7783-06-04) in the atmosphere;

wherein the oxygen sensor measures the concentration of diatomic oxygen (CAS 7782-44-7) in the atmosphere;

wherein the ozone sensor measures the concentration of ozone (CAS 10028-15-6) in the atmosphere;

wherein the carbon monoxide sensor measures the concentration of carbon monoxide (CAS 630-08-0) in the atmosphere;

wherein the carbon dioxide sensor measures the concentration of carbon dioxide (CAS 124-38-9) in the atmosphere;

wherein the ammonia sensor measures the concentration of ammonia (CAS 7664-41-7) in the atmosphere;

the nitrogen dioxide sensor measures the concentration of nitrogen dioxide (CAS 10102-44-0) in the atmosphere;

wherein the alkanes sensor measures the concentration of alkanes in the atmosphere;

wherein the particulates sensor measures the concentration of particulates in the atmosphere.

6. The instrument according to claim 5
wherein the plurality of compensation sensors comprises a temperature sensor, a humidity sensor, and a pressure sensor;
wherein the temperature sensor measures the temperature of the atmosphere;
wherein the humidity sensor measures the humidity of the atmosphere;
wherein the pressure sensor measures the pressure of the atmosphere;
wherein the readings collected from the plurality of compensation sensors are used by the control system to adjust the measurements taken by each of the plurality of gas sensors to compensate for known measurement variations created by environmental conditions.

7. The instrument according to claim 6
wherein the spectrometer is an electrical device;
wherein the spectrometer reflects one or more beams of electromagnetic radiation of known frequencies through the atmospheric sample and measures the spectrum of the returned beam;
wherein the spectrometer transmits the measured spectrum of the returned beam to the control system;
wherein the control system performs a spectral analysis on the return beam data.

8. The instrument according to claim 7
wherein the spectrometer comprises a light source, a light sensor, a reflective surface, and a spectral circuit;
wherein the light source comprises one or more LEDs that are incorporated into the spectrometer;
wherein the light source is calibrated to emit electromagnetic radiation at one or more previously determined wavelengths;
wherein the light sensor is a sensor that is calibrated to detect electromagnetic radiation over a range of previously determined frequencies;
wherein the light sensor receives the electromagnetic radiation generated by the light source after the electromagnetic radiation has passed through the atmospheric gas sample;
wherein the reflective surface is a mirrored structure that reflects the light generated by the light source to the light sensor as the generated light is passing through the atmospheric gases;
wherein the spectral circuit is an electrical circuit incorporated into the spectrometer for the purpose of subdividing the received light into spectral ranges for analysis by the logic module.

9. The instrument according to claim 8
wherein the control system is an electrical device;
wherein the control system comprises a logic module, a communication module, a display, a plurality of LEDs, a plurality of switches, a battery and a diode;
wherein the logic module, the communication module, the display, the plurality of LEDs, the plurality of switches, the battery and the diode are electrically interconnected.

10. The instrument according to claim 9
wherein the logic module is a programmable electronic device that manages, regulates, and operates the control system;
wherein the logic module monitors each of the plurality of gas sensors;
wherein the logic module monitors each of the plurality of compensation sensors;
wherein the logic module monitors calculates a compensated concentration level of each of the plurality of potentially hazardous gases based on the readings from both the plurality of gas sensors and the plurality of compensation sensors;
wherein the logic module compares the compensated concentration levels of each of the plurality of potentially hazardous gases against a predetermined exposure level;
wherein the logic module displays the calculated compensated concentration levels for each of the plurality of potentially hazardous gases on the display;
wherein the logic module generates an alert using the plurality of LEDs should a gas selected from the plurality of potentially hazardous gases exceed the predetermined exposure limit;
wherein the logic module transmits the calculated compensation concentration levels to the ACARS;
wherein the logic module monitors the plurality of switches.

11. The instrument according to claim 10
wherein the communication module is a wireless electronic communication device;
wherein the communication module establishes a hardwired first communication link with the ACARS;

wherein the communication module establishes a wireless second communication link in order to transmit data collected from the plurality of gas sensors to the ACARS;

wherein the communication module that allows the logic module to wirelessly communicate with a locally presented personal data device using a third communication link.

12. The instrument according to claim 11
wherein the display is an LCD
wherein the LCD is mounted in the shell;
wherein the logic module uses the LCD to display the calculated compensated concentration levels of each of the monitored gases.

13. The instrument according to claim 12
wherein the battery is a rechargeable battery;
wherein the docking station provides an electrical circuit that reverses the polarity of the battery;
wherein the docking station attaches to the ACARS from which it draws electrical energy;
wherein the diode is an electrical device that allows electric current to flow in only one direction;
wherein the diode is installed between the battery and the docking station such that electricity will not flow from the positive terminal of the battery to the positive terminal of the plug.

14. The instrument according to claim 13
wherein each of the plurality of LEDs is an electrical device;
wherein each of the plurality of switches is an electrical device;
wherein the plurality of LEDs comprises a first LED, a second LED, a third LED, and a fourth LED;
wherein the first LED indicates that the gas monitor is available for operation;
wherein the second LED indicates that the testing procedures are in process;
wherein the third LED indicates that the logic module has generated an alert;
wherein the fourth LED indicates that the logic module has generated an alert that requires immediate attention;
wherein the plurality of switches comprises a first switch, a second switch, and a third switch;
wherein the first switch is a momentary switch;
wherein the first switch instructs the logic module to initiate operation;
wherein the second switch is a momentary switch;
wherein the second switch instructs the logic module to initiate testing operations;
wherein the third switch is a momentary switch;
wherein the third switch is instructs the logic module to transmit the calculated compensated concentration levels, the spectral analysis data, and the alerts to the ACARS and the personal data device.

15. The instrument according to claim 14
wherein the docking station comprises a stanchion, a base, a cap, and a plug;
wherein the stanchion attaches the base to the cap;
wherein the plug attaches to the base;
wherein the docking station is a rectilinear structure;
wherein the docking station stores the gas monitor when not in use;
wherein the docking station recharges the battery during storage of the gas monitor;
wherein the docking station provides the first communication link between the gas monitor and the ACARS.

16. The instrument according to claim 15
wherein the stanchion is a rectangular plate;
wherein the stanchion attaches the base to the cap;
wherein the stanchion attaches to a bulkhead within the aircraft;
wherein the base is a horizontal surface;
wherein the base projects perpendicularly away from the stanchion;
wherein the cap is a horizontal surface;
wherein the cap projects perpendicularly away from the stanchion;
wherein the cap projects in the same direction as the base;
wherein the cap attaches to the end of the stanchion that is distal from the base;
wherein the plug is an electrical termination that is matched to the port of the gas monitor;
wherein the plug electrically connects the gas monitor to the ACARS such that electrical power and data may be exchanged between the gas monitor and the ACARS.

* * * * *